United States Patent
Strein et al.

(10) Patent No.: US 11,864,976 B2
(45) Date of Patent: *Jan. 9, 2024

(54) ROTATABLE SURGICAL TABLE

(71) Applicant: Regeneron Pharmaceuticals, Inc., Tarrytown, NY (US)

(72) Inventors: John Strein, Danbury, CT (US); Sam Cichon, Fishkill, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 792 days.

This patent is subject to a terminal disclaimer.

(21) Appl. No.: 16/936,831

(22) Filed: Jul. 23, 2020

(65) Prior Publication Data
US 2020/0352691 A1    Nov. 12, 2020

Related U.S. Application Data

(63) Continuation of application No. 15/875,716, filed on Jan. 19, 2018, now Pat. No. 10,758,331.
(Continued)

(51) Int. Cl.
*A61D 3/00* (2006.01)
*A61G 13/02* (2006.01)
(Continued)

(52) U.S. Cl.
CPC .............. *A61D 3/00* (2013.01); *A61D 7/04* (2013.01); *A61G 13/02* (2013.01);
(Continued)

(58) Field of Classification Search
CPC ............ A61G 13/02–08; A61G 13/102; A61G 13/105; A61G 13/00; A61D 7/04;
(Continued)

(56) References Cited

U.S. PATENT DOCUMENTS

| 809,358 A | 1/1906 | Conkey |
| 3,318,597 A * | 5/1967 | Jamalabo ................. A61D 3/00 5/621 |

(Continued)

FOREIGN PATENT DOCUMENTS

| CN | 203315265 U | 12/2013 |
| CN | 102755202 B | 1/2015 |

OTHER PUBLICATIONS

PCT/US2018/014325 International Search Report and Written Opinion dated Jun. 21, 2018.
(Continued)

*Primary Examiner* — Joseph D. Boecker
*Assistant Examiner* — Thomas W Greig
(74) *Attorney, Agent, or Firm* — Alston & Bird LLP; Yongjin Choi

(57) ABSTRACT

Provided is a rotatable surgical apparatus and accompanying method for processing a specimen via the rotatable surgical apparatus. The surgical apparatus may include a base member and a platform member where the platform member and base member abut. Each of the base member and platform member may define one or more channel. The one or more base channels may be in fluid communication with the one or more platform channels. A nozzle may be disposed on the top surface of the platform member, in fluid communication with the at least one platform channel and may administer anesthetic to a specimen.

19 Claims, 15 Drawing Sheets

Related U.S. Application Data

(60) Provisional application No. 62/448,710, filed on Jan. 20, 2017.

(51) Int. Cl.
*A61M 16/00* (2006.01)
*A61D 7/04* (2006.01)

(52) U.S. Cl.
CPC ....... *A61M 16/009* (2013.01); *A61G 2210/00* (2013.01); *A61M 2250/00* (2013.01)

(58) Field of Classification Search
CPC ....... A61D 3/00; A61M 16/009; A61M 16/01; A61M 16/104
See application file for complete search history.

(56) References Cited

U.S. PATENT DOCUMENTS

| | | | |
|---|---|---|---|
| 3,548,840 A | 12/1970 | Baumgarter | |
| 3,687,137 A * | 8/1972 | Johnson | A61M 16/18 128/205.28 |
| 4,332,244 A * | 6/1982 | Levy | A61D 7/04 128/206.28 |
| 4,794,921 A | 1/1989 | Lindkvist | |
| 4,807,617 A | 2/1989 | Nesti | |
| 5,297,502 A * | 3/1994 | Jaeger | A61D 7/04 119/420 |
| 6,776,158 B1 * | 8/2004 | Anderson | A61M 16/0093 119/419 |
| 8,905,585 B2 * | 12/2014 | Dallam | A61G 10/02 362/276 |
| 9,056,841 B2 | 6/2015 | Pomper et al. | |
| 9,129,043 B2 | 9/2015 | Nawana et al. | |
| 10,758,331 B2 | 9/2020 | Strein et al. | |
| 10,793,874 B2 | 10/2020 | Frendewey et al. | |
| 2009/0126113 A1 | 5/2009 | Hejkal et al. | |
| 2013/0213318 A1 | 8/2013 | Katz | |
| 2014/0069426 A1 * | 3/2014 | Houts | A61M 16/0057 128/203.29 |
| 2016/0000627 A1 | 1/2016 | Jackson et al. | |
| 2016/0222016 A1 | 8/2016 | Castro et al. | |

OTHER PUBLICATIONS

U.S. Appl. No. 15/875,716 Notice of Allowance dated Jun. 18, 2020.

PCT/US2018/014325 International Preliminary Report on Patentability dated Jul. 23, 2019.

* cited by examiner

ROTATABLE SURGICAL TABLE

CROSS-REFERENCE TO RELATED APPLICATIONS

This patent application is a continuation of U.S. patent application Ser. No. 15/875,716, filed Jan. 19, 2018, which claims priority from Provisional Application Ser. No. 62/448,710, filed Jan. 20, 2017. The contents of both of which are incorporated herein by reference in their entirety.

BACKGROUND OF THE INVENTION

Surgical tables and associated systems for examining and operating on specimens, which may include rodents and other small animals, provide support and stability for performing delicate procedures. Surgical procedures are often paired with anesthesia as a means to reduce the pain of the subject as well ensure stability throughout the procedure by reducing the movement of the subject.

Traditionally, a subject or specimen was secured to a stationary object and administered anesthesia through a separate source such as by injectable or inhalable means. Additionally, once secured, the specimen could only be moved through contact with the specimen. This current process of adjusting a specimen is cumbersome and inefficient providing slower procedure times and increased costs. Conventional surgical apparatuses and associated methods also fail to allow for easy access to the specimen from various angles during a procedure.

Applicant has identified a number of additional deficiencies and problems associated with conventional surgical tables and associated systems and methods. Through applied effort, ingenuity, and innovation, many of these identified problems have been solved by developing solutions that are included in embodiments of the present invention, many examples of which are described in detail herein.

BRIEF SUMMARY OF THE INVENTION

The apparatus and methods described herein provide a rotatable surgical table capable of supplying an anesthetic to a specimen wherein the flow of anesthesia is maintained when the table is rotated.

In some embodiments, a surgical table is provided where the surgical table comprises a base member defining a first surface and at least one base channel. The surgical table may also comprise a platform member defining a top surface and a bottom surface, wherein the bottom surface may be configured to abut the first surface of the base member, wherein the platform member may define at least one platform channel, wherein the at least one platform channel and the at least one base channel are in fluid communication, and wherein the platform member may be configured to rotate relative to the base member while maintaining said fluid communication. The surgical table may also define a nozzle disposed on the top surface on the platform member, wherein the nozzle is in fluid communication with the at least one platform channel.

In some embodiments, the at least one base channel of the base member may further comprise a first base channel and a second base channel, and the at least one platform channel may comprise a first platform channel and a second platform channel.

In some embodiments, the nozzle may define an inner shell in continuous fluid communication with a first platform channel and an outer shell in fluid communication with a second platform channel creating a self-scavenging system.

In some embodiments, at least one of the base member and platform member of the surgical table may be configured to connect the at least one base channel with the at least one platform channel.

In some embodiments, the surgical table may further comprise one or more walls disposed between the first surface of the base member and the bottom surface of the platform member, wherein the one or more walls may be configured to maintain fluid communication between the at least one channel of the base member and the at least one channel of the platform member.

In some embodiments, at least one of the bottom surface of the platform member and the first surface of the base member may define two concentric annular walls. In such a case, in some embodiments, one or more gaskets are disposed between the first surface of the base member and the bottom surface of the platform member, wherein the one or more gaskets abut the two concentric annular walls.

In some still further embodiments, the base member and the platform member may define a first annular chamber bounded by an innermost wall of the concentric annular walls and a second annular chamber disposed between the two concentric annular walls such that the first channel of the platform member and the first channel of the base member may be configured to be in continuous fluid communication and the second channel of the base member and the second channel of the platform member may be configured to be in continuous fluid communication.

In some embodiments, one or more gaskets may be disposed between the first surface of the base member and the bottom surface of the platform member.

In some embodiments, the base member further may define one or more side ports configured to create a fluid connection between an input source and the at least one base channel.

In some embodiments, a method for processing a specimen via a surgical apparatus is provided where the method comprises providing a base member defining a first surface, wherein the base member defines at least one base channel; providing a platform member defining a top surface and a bottom surface, wherein the bottom surface is configured to abut the first surface of the base member, wherein the platform member defines at least one platform channel, wherein the at least one platform channel and the at least one base channel are in fluid communication, wherein the platform member is configured to rotate relative to the base member while maintaining said fluid communication; providing a nozzle disposed on the top surface on the platform member, wherein the nozzle is in fluid communication with the at least one platform channel; affixing a specimen to a surgical apparatus; and supplying an anesthetic to one of the base channel, wherein the anesthetic is configured to flow from the at least one base channel to the at least one platform channel and from the at least one platform channel to the nozzle such that the anesthetic is administered to the specimen.

In some embodiments, the at least one base channel of the base member may further comprise a first base channel and a second base channel, and the at least one platform channel may comprise a first platform channel and a second platform channel.

In some embodiments, the nozzle may define an inner shell in continuous fluid communication with a first platform channel and an outer shell in fluid communication with a second platform channel creating a self-scavenging system.

In some embodiments, at least one of the base member and platform member of the surgical table may be configured to connect the at least one base channel with the at least one platform channel.

In some embodiments, the method may further comprise disposing one or more walls between the first surface of the base member and the bottom surface of the platform member, wherein the one or more walls may be configured to maintain fluid communication between the at least one channel of the base member and the at least one channel of the platform member.

In some embodiments, at least one of the bottom surface of the platform member and the first surface of the base member may define two concentric annular walls. In such a case, in some embodiments, one or more gaskets are disposed between the first surface of the base member and the bottom surface of the platform member, wherein the one or more gaskets abut the two concentric annular walls.

In some still further embodiments, the base member and the platform member may define a first annular chamber bounded by an innermost wall of the concentric annular walls and a second annular chamber disposed between the two concentric annular walls such that the first channel of the platform member and the first channel of the base member may be configured to be in continuous fluid communication and the second channel of the base member and the second channel of the platform member may be configured to be in continuous fluid communication.

In some embodiments, one or more gaskets may be disposed between the first surface of the base member and the bottom surface of the platform member.

In some embodiments, the base member further may define one or more side ports configured to create a fluid connection between an input source and the at least one base channel.

BRIEF DESCRIPTION OF THE SEVERAL VIEWS OF THE DRAWINGS

Figure 1:
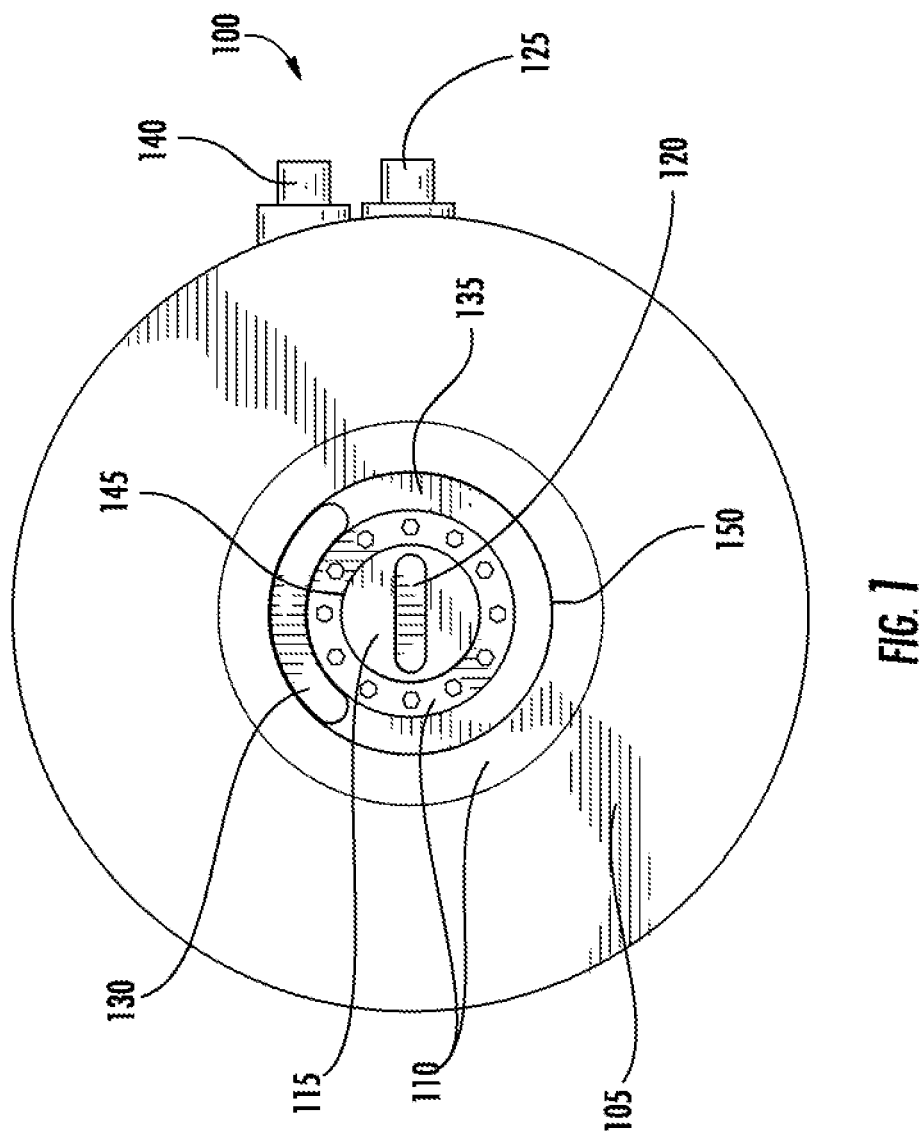
Figure 2:
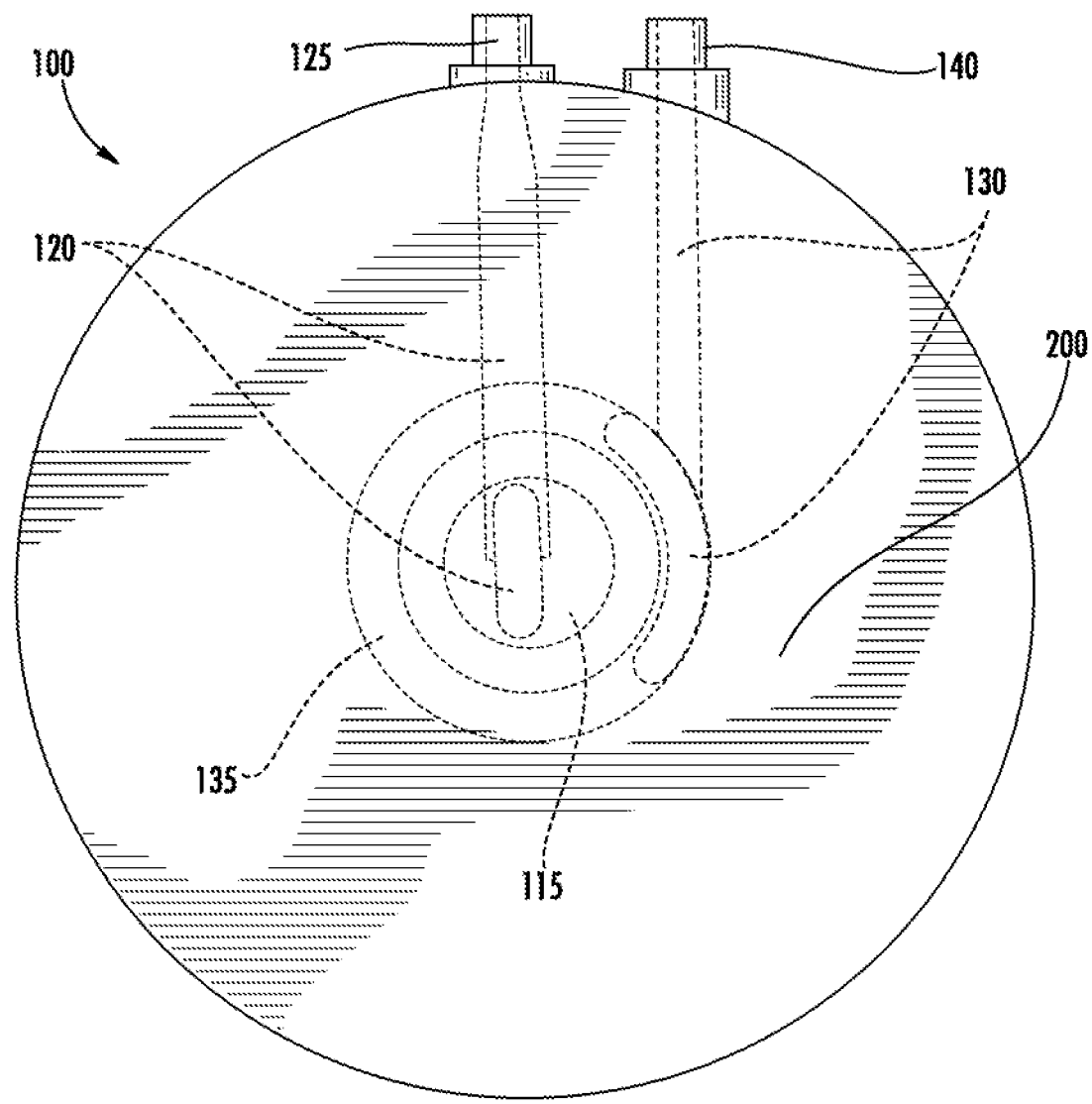
Figure 3:
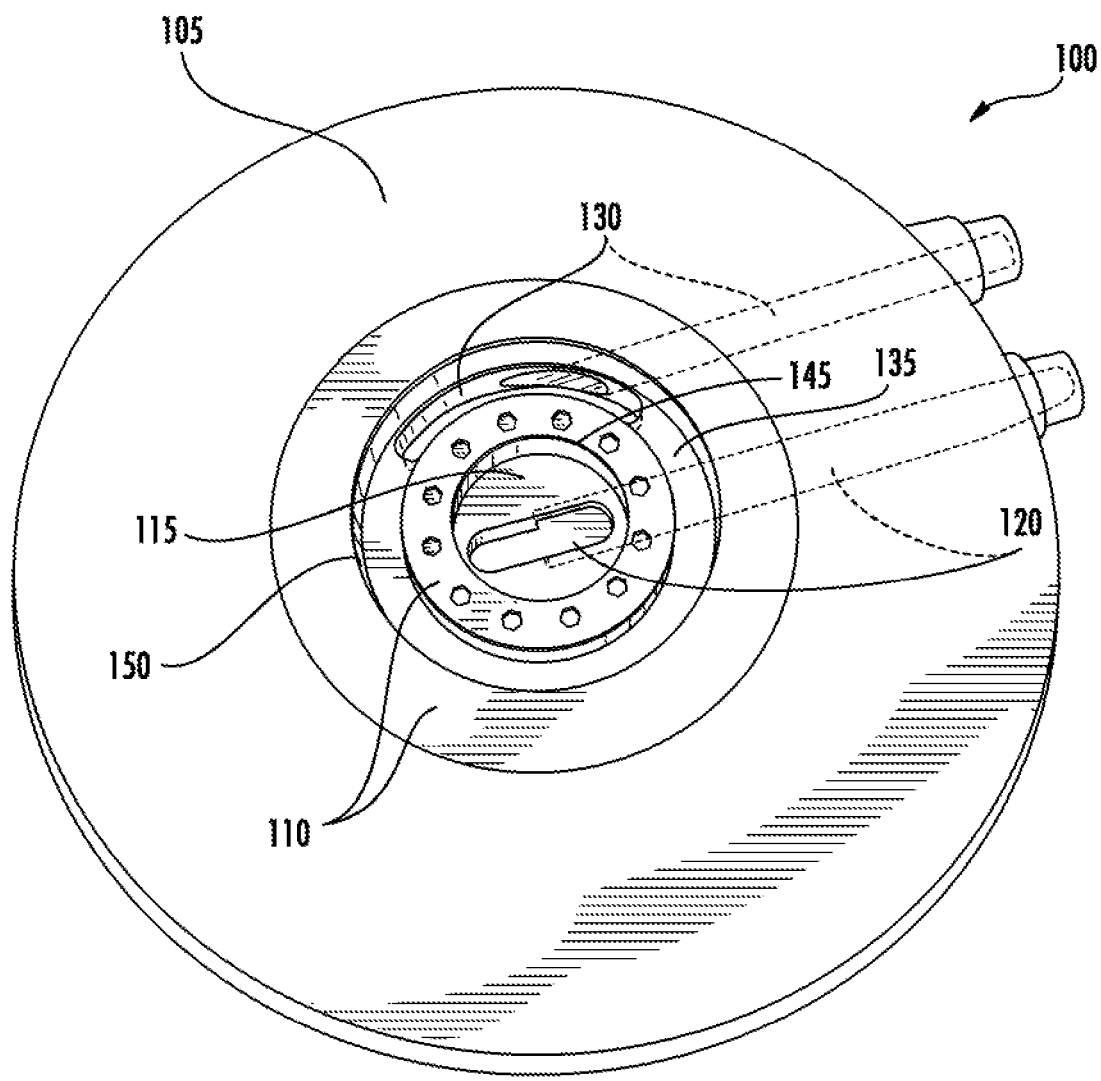
Figure 4:
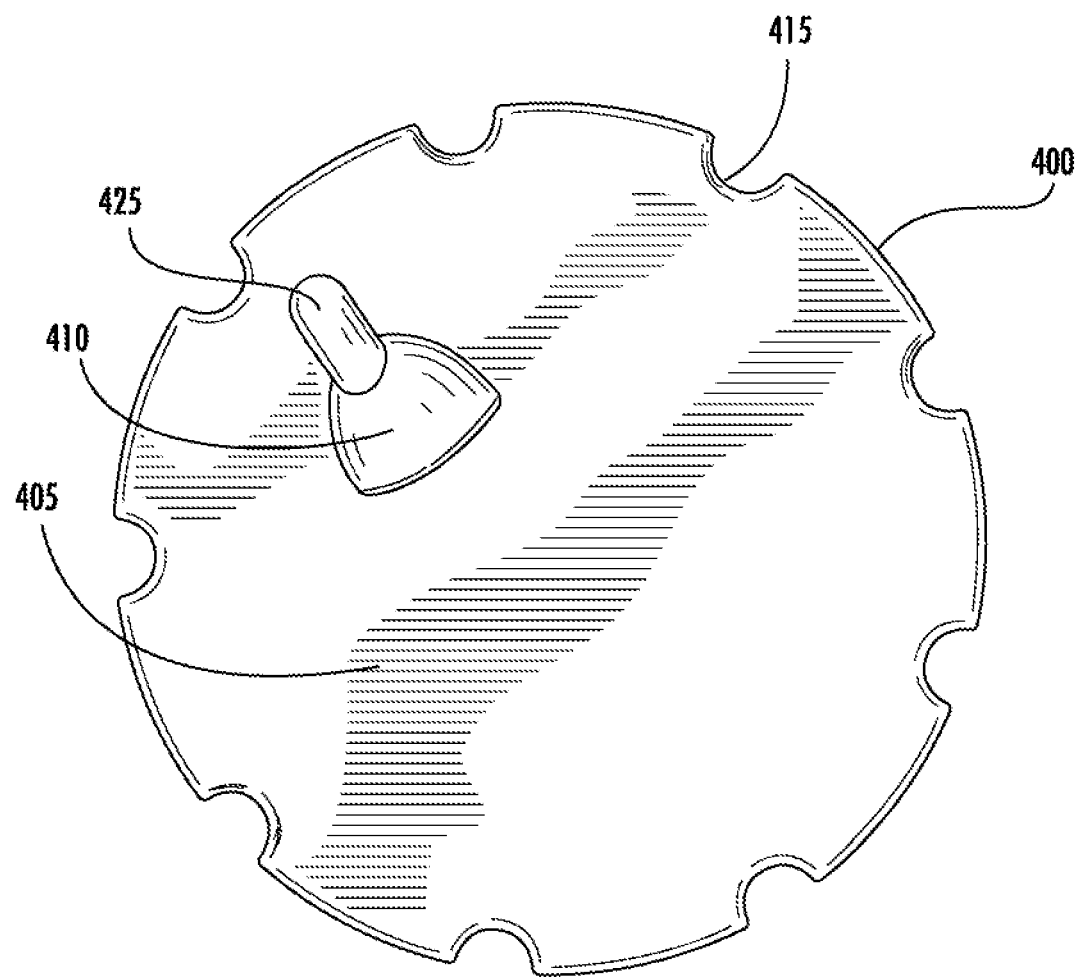
Figure 5:
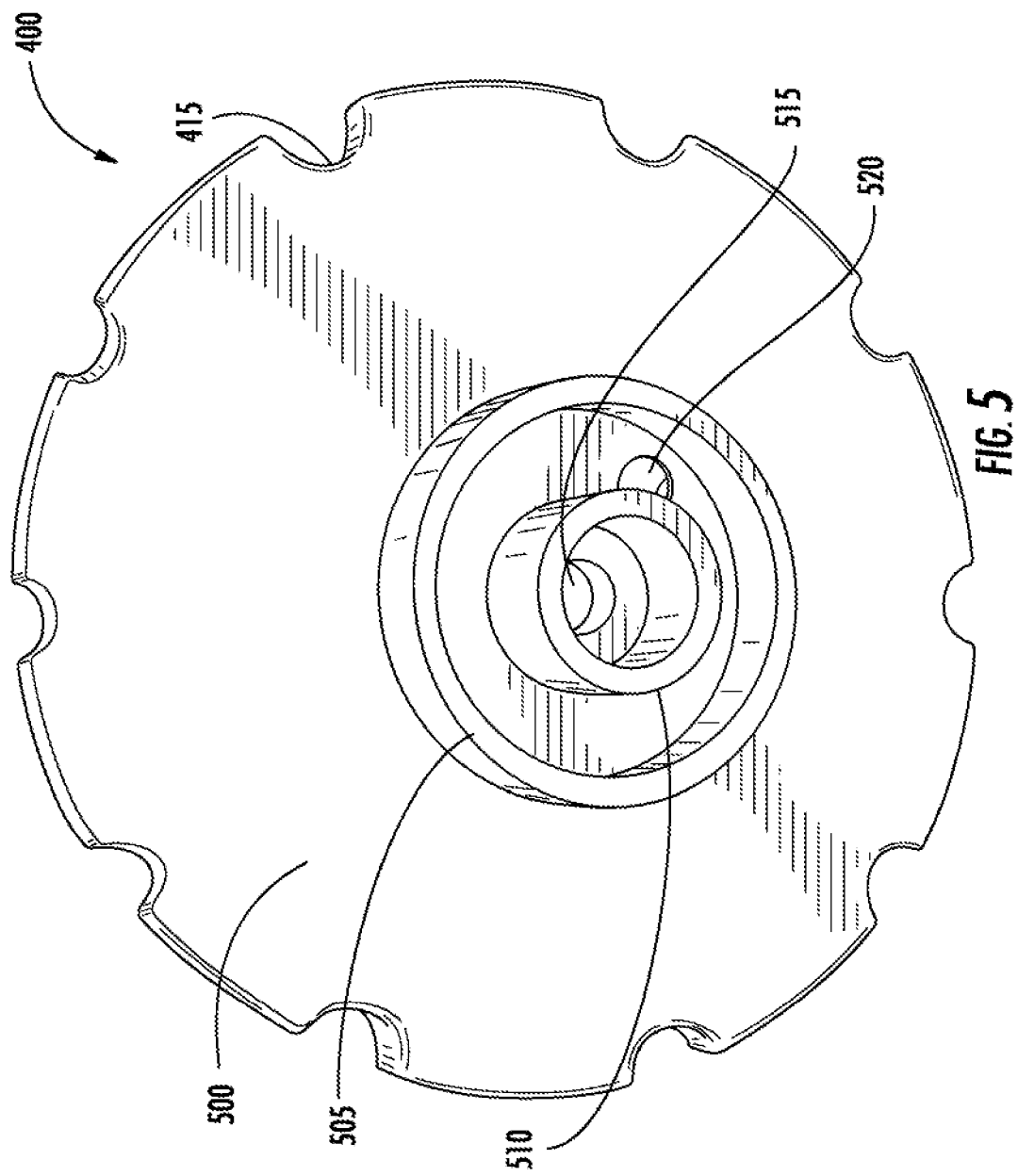
Figure 6:
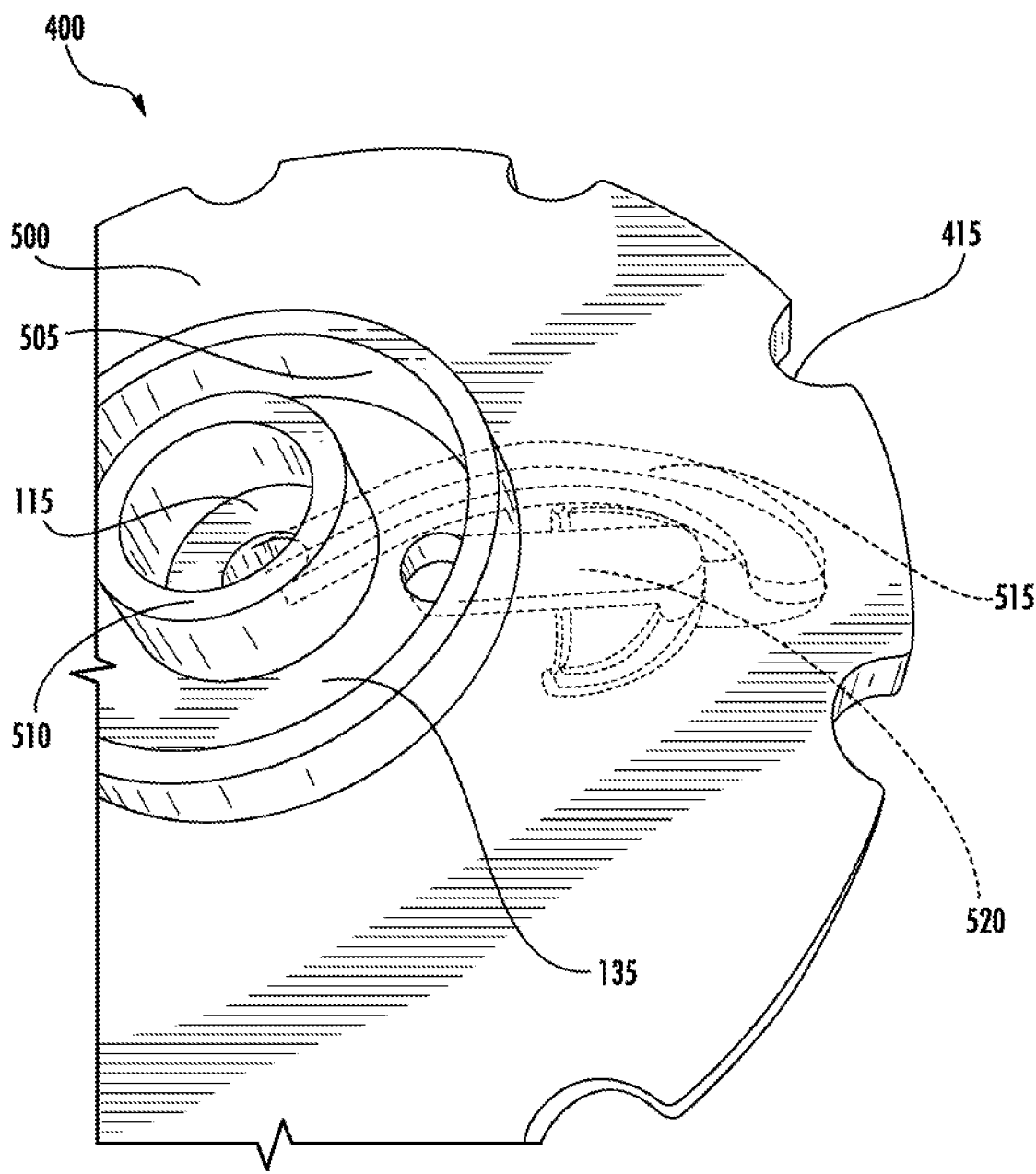
Figure 7:
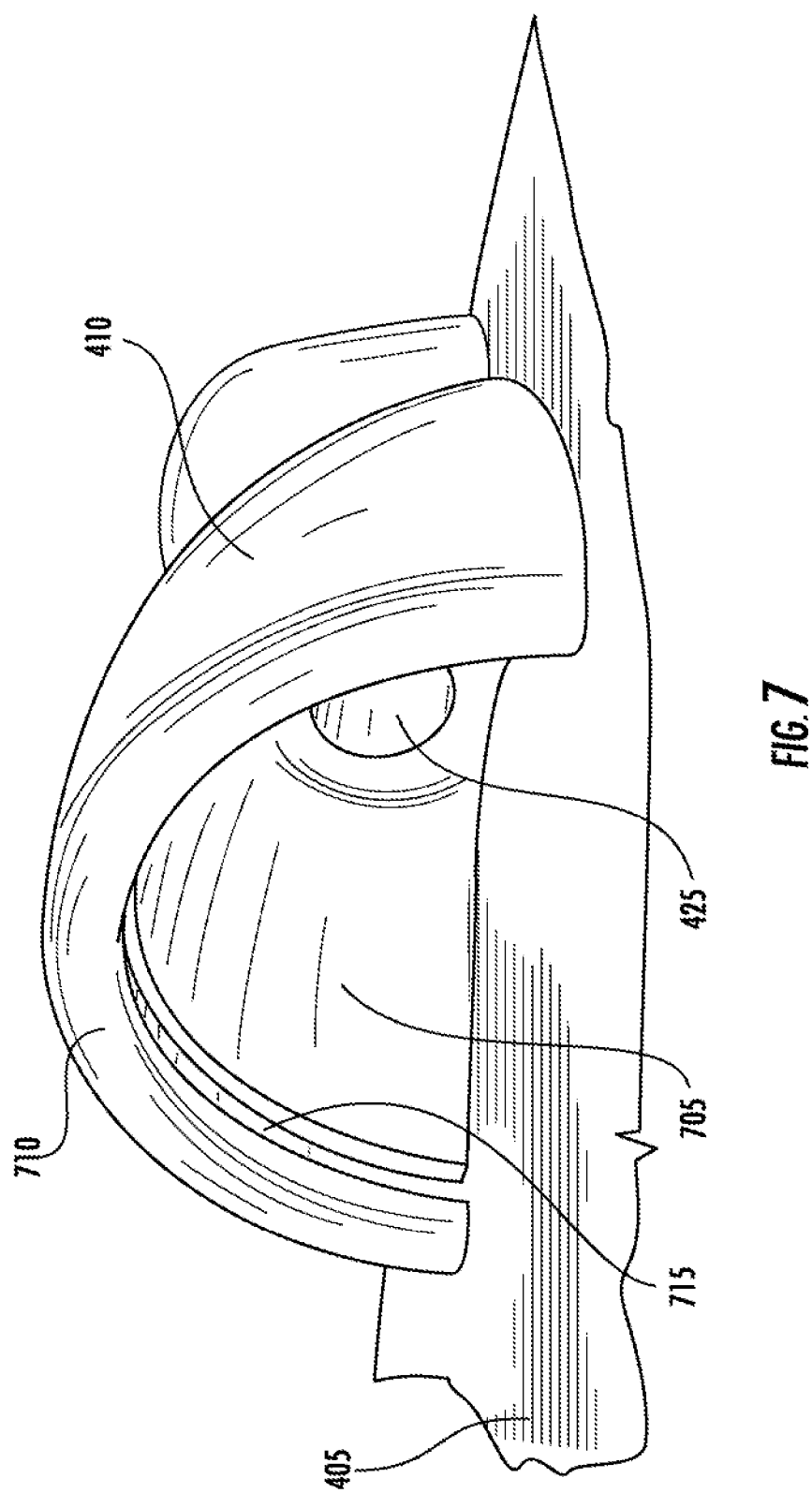
Figure 8:
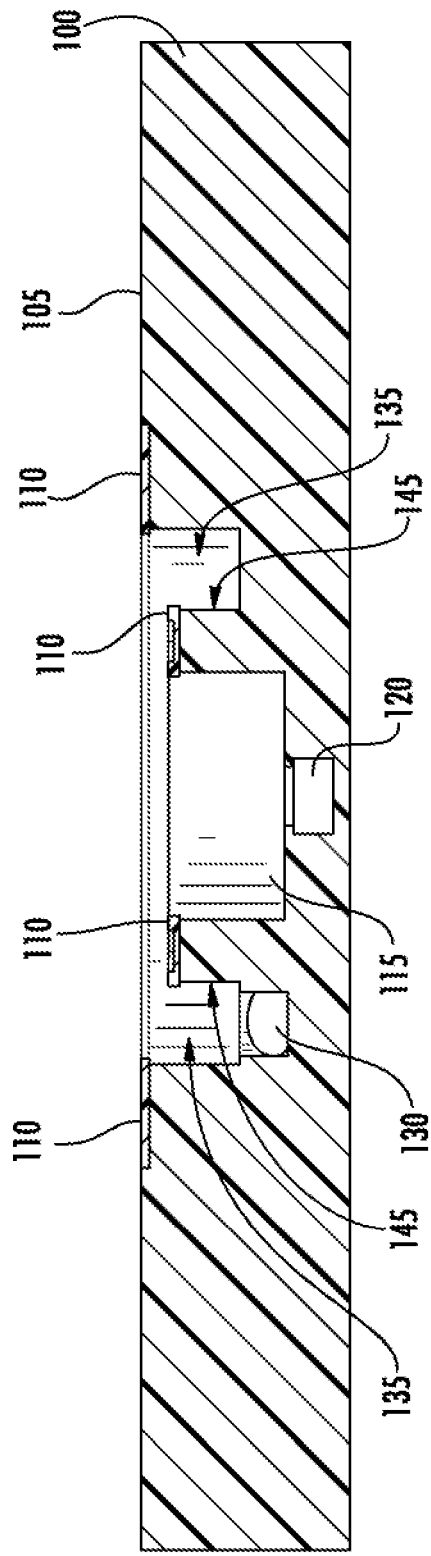
Figure 9:
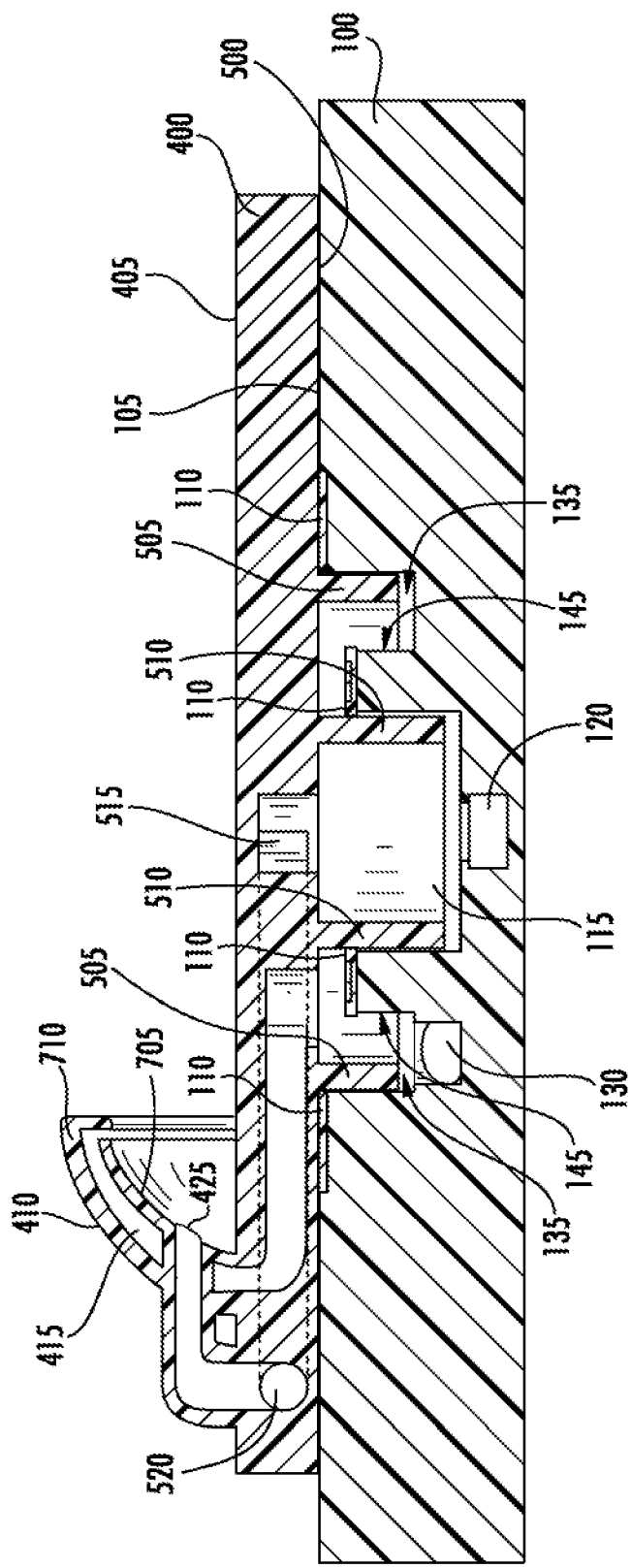
Figure 10:
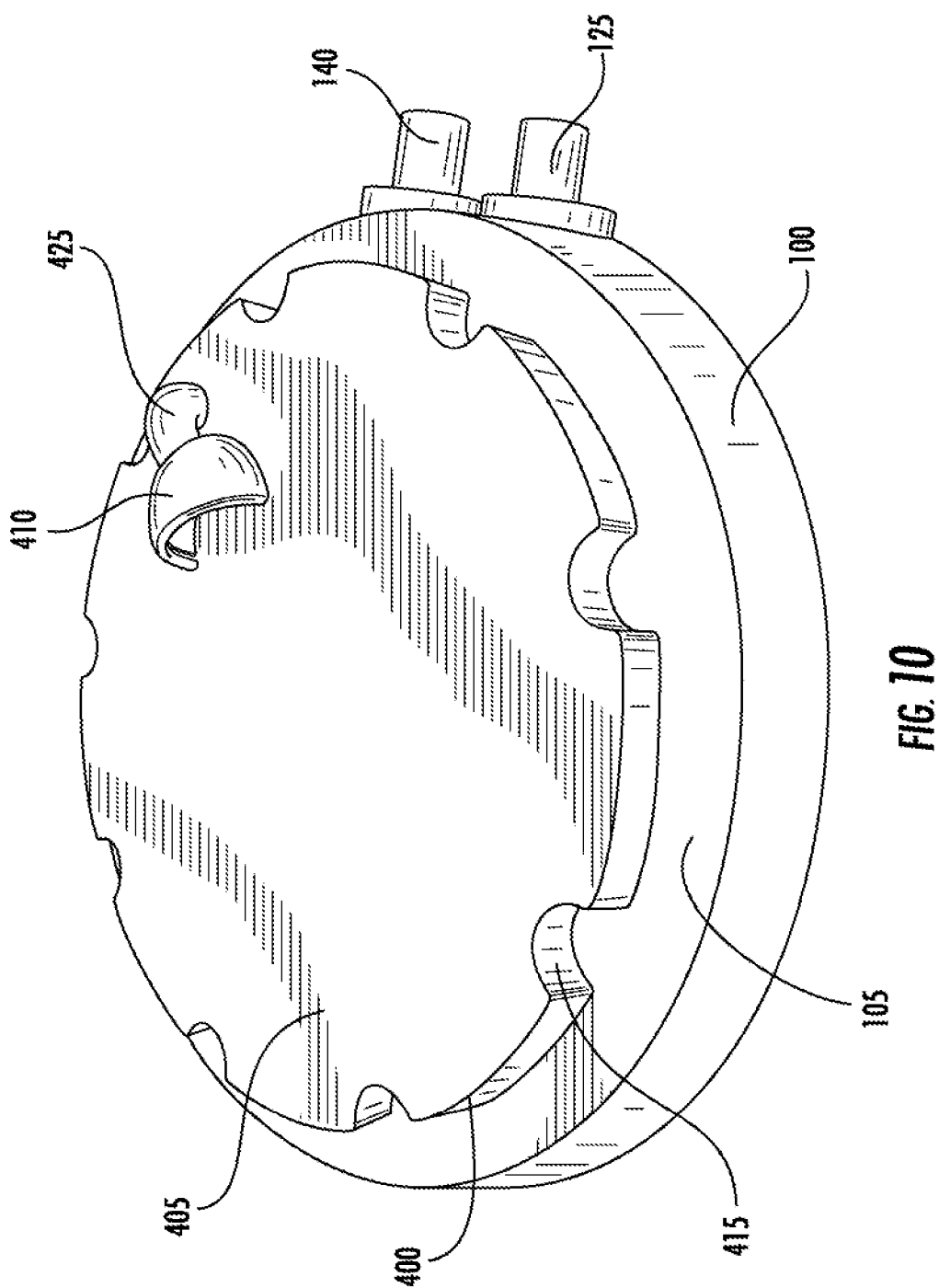
Figure 11:
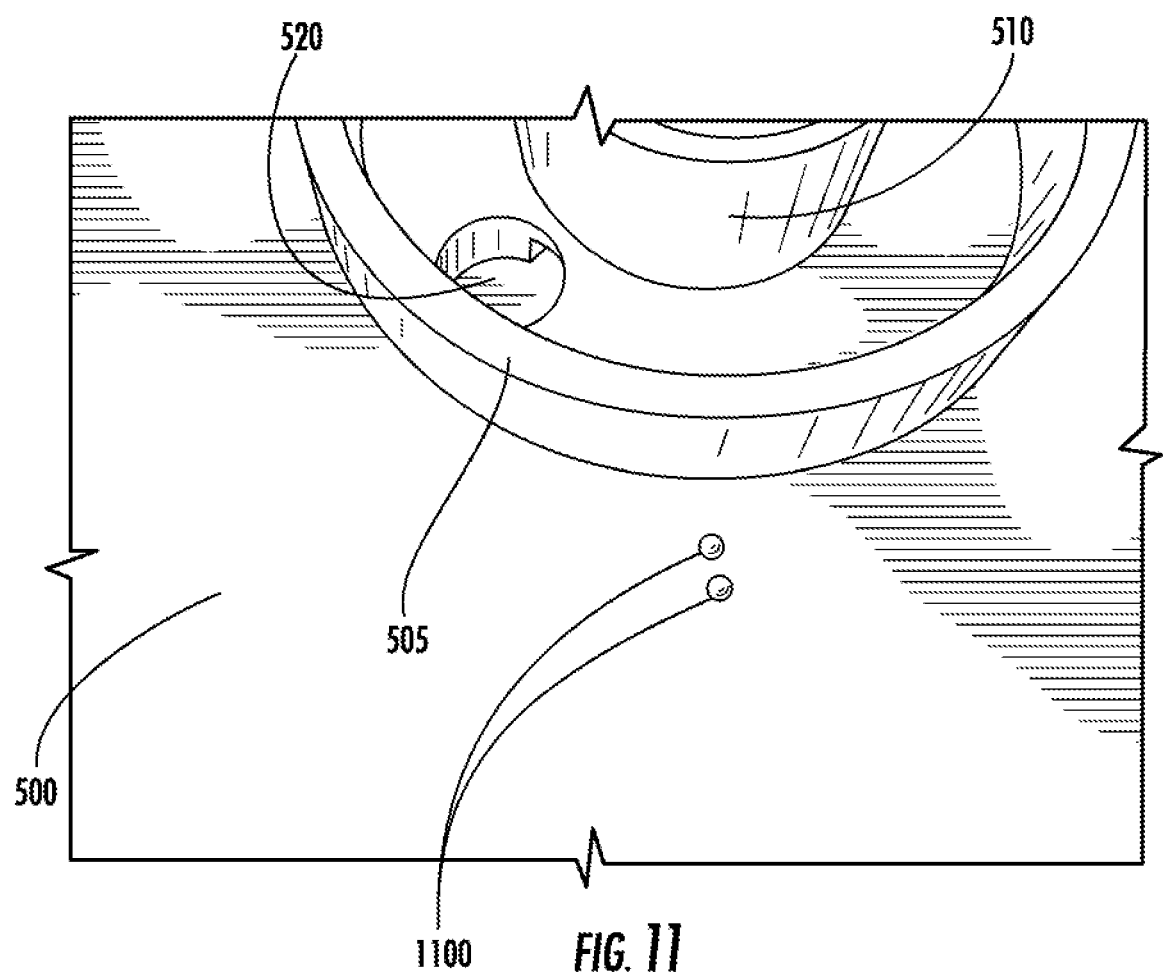
Figure 12:
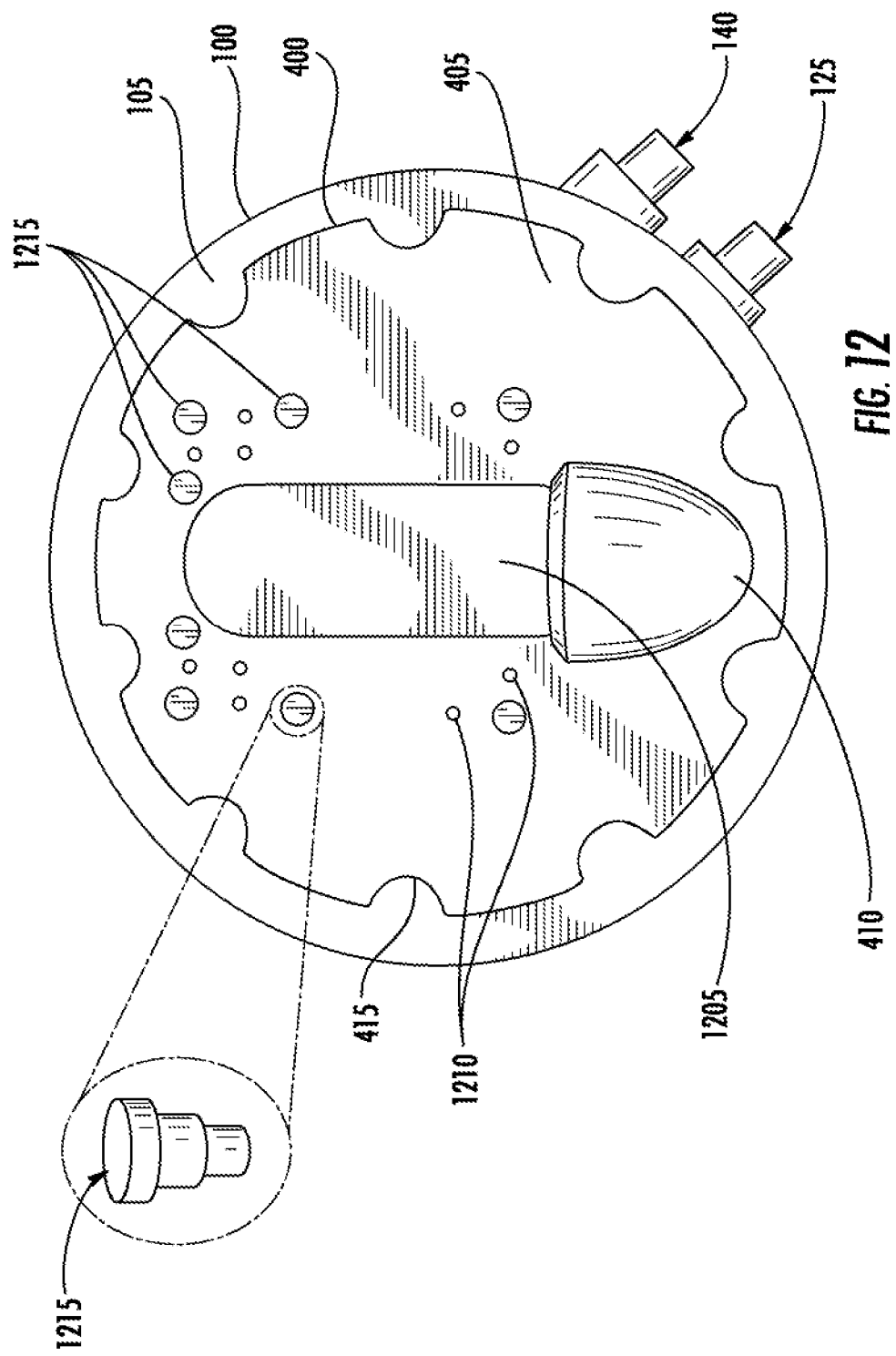
Figure 13:
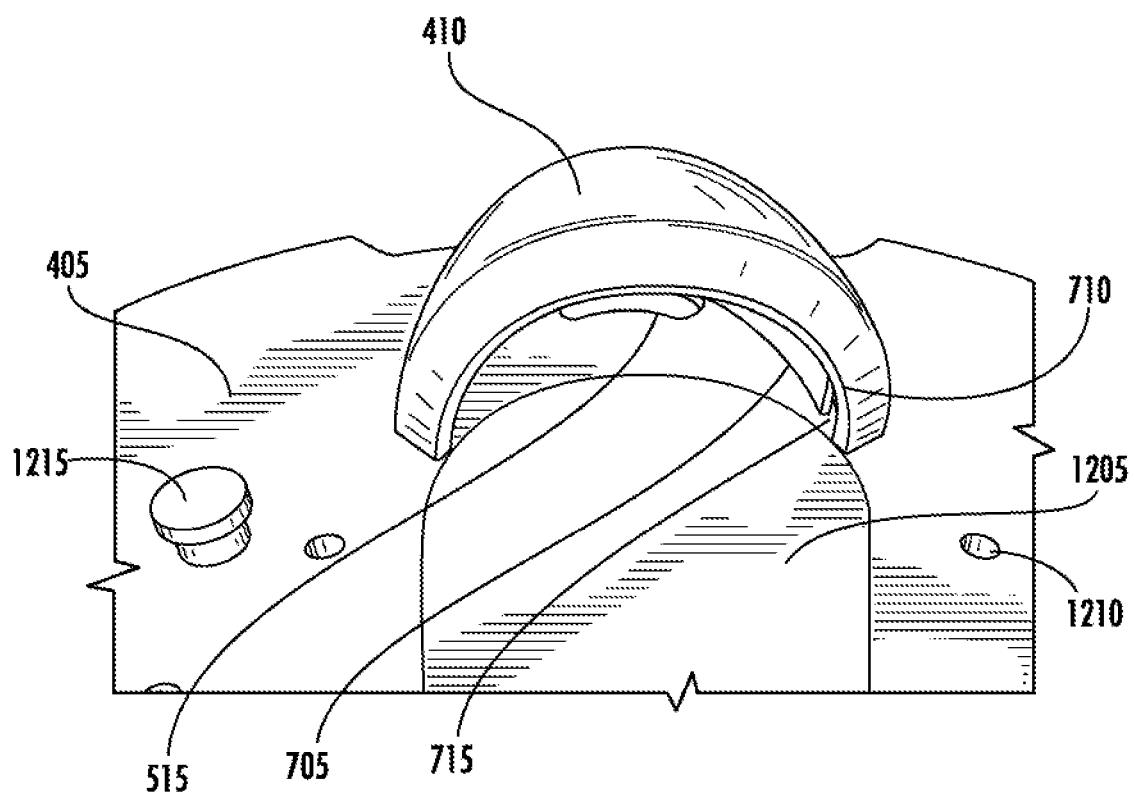
Figure 14:
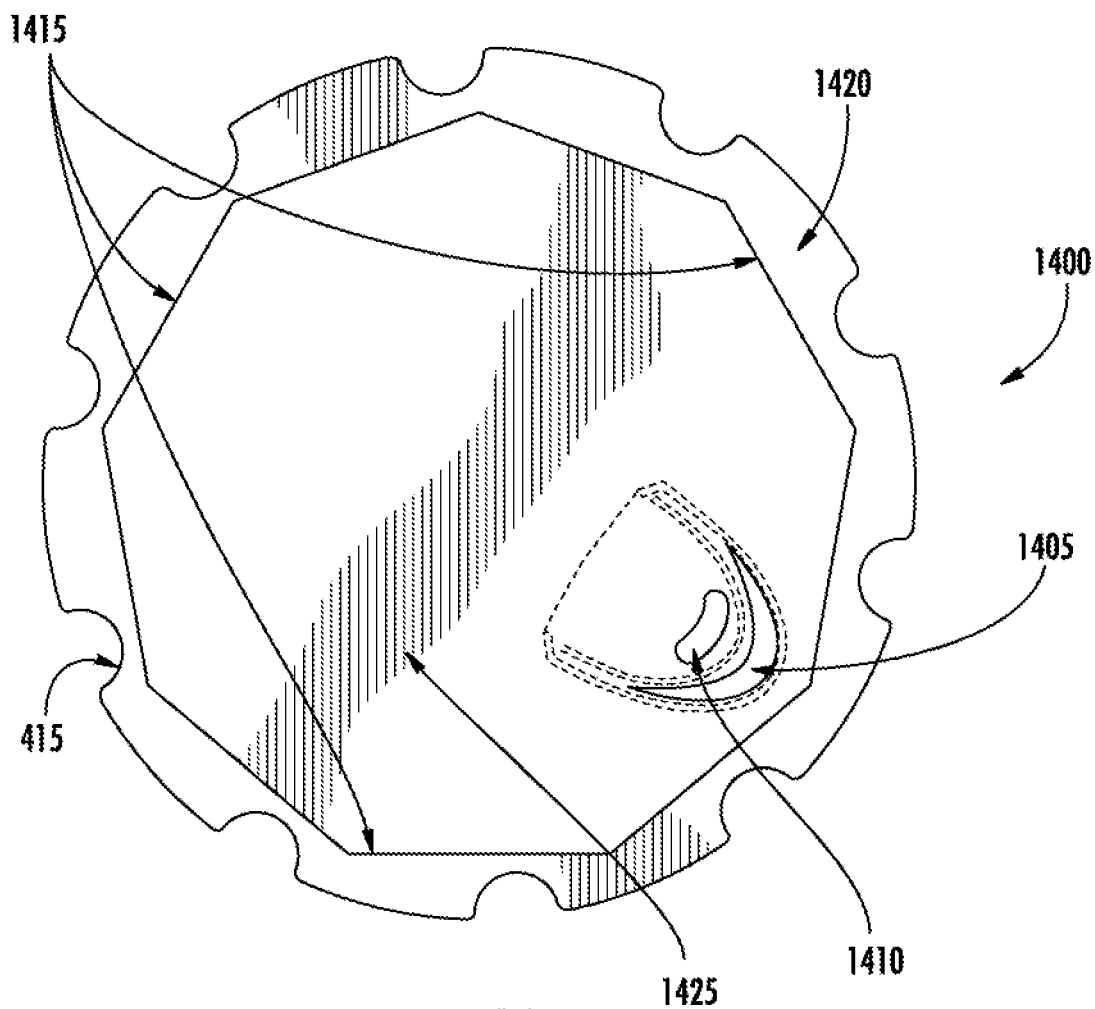
Figure 15:
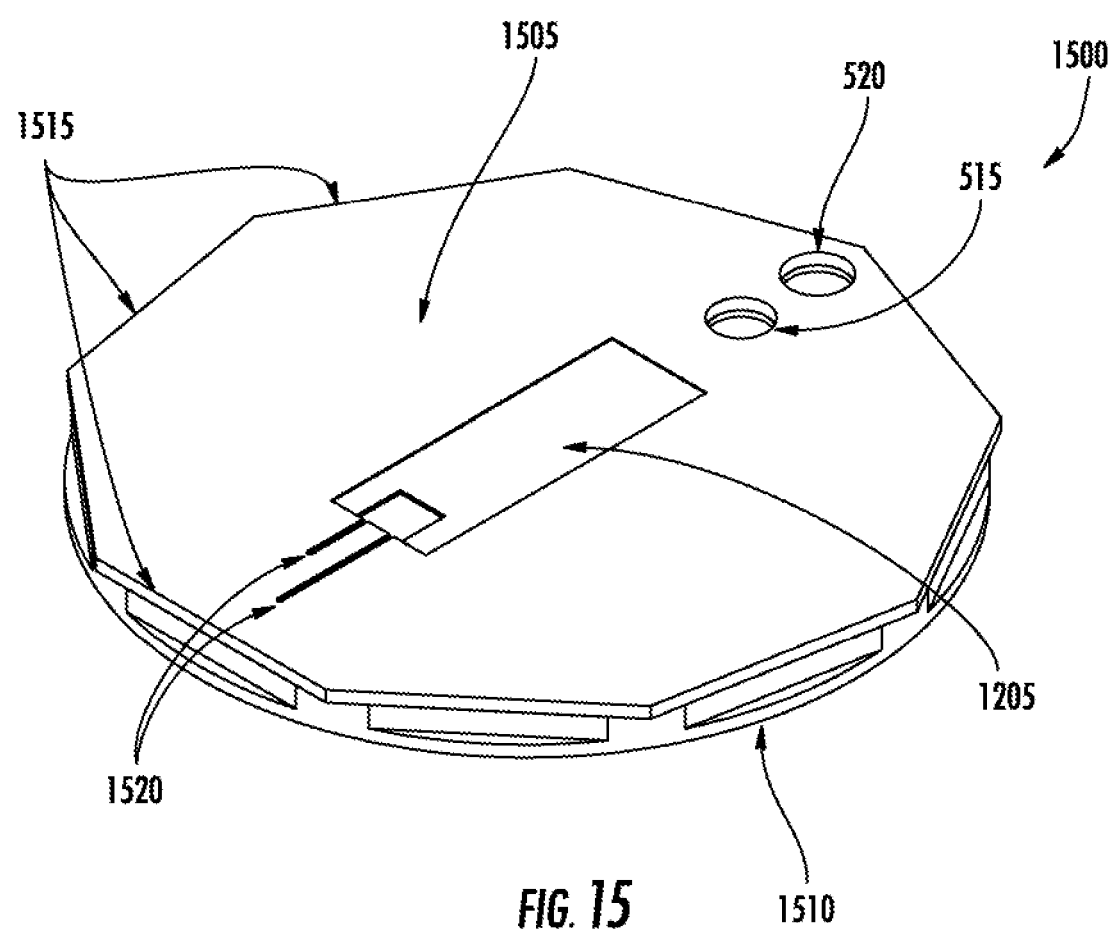

Having thus described the invention in general terms, reference will now be made to the accompanying drawings, which are not necessarily drawn to scale, and wherein:

FIG. 1 illustrates a top view of a base member of a surgical apparatus, in accordance with some embodiments discussed herein;

FIG. 2 illustrates a bottom view of the base member of FIG. 1;

FIG. 3 illustrates a top view of the base member of FIG. 1;

FIG. 4 illustrates a top view of a platform member of a surgical apparatus, in accordance with some embodiments discussed herein;

FIG. 5 illustrates a bottom view of the platform member of FIG. 4;

FIG. 6 illustrates a bottom view of the platform member of FIG. 4;

FIG. 7 illustrates a nozzle, in accordance with some embodiments discussed herein;

FIG. 8 illustrates a cross-sectional side view of the base member of FIG. 1;

FIG. 9 illustrates a cross-sectional side view of the platform and base members of FIGS. 1 and 4;

FIG. 10 illustrates the rotatable surgical table, in accordance with some embodiments discussed herein;

FIG. 11 illustrates a bottom view of an alternative platform member, in accordance with some embodiments discussed herein;

FIG. 12 illustrates a top view of a platform member of FIG. 11 in conjunction with a base member;

FIG. 13 illustrates a nozzle, in accordance with some embodiments discussed herein;

FIG. 14 illustrates a bottom view of a top portion of an alternative platform member, in accordance with some embodiments discussed herein; and FIG. 15 illustrates a perspective view of a bottom portion of an alternative platform member, in accordance with some embodiments discussed herein.

DETAILED DESCRIPTION

Overview

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

In the development of new medical procedures, medications, and other treatment options, rodents (i.e., rats, mice, etc.) are often utilized as a medium for verifying the safety and effectiveness of new developments before administration to human subjects. Rodents are often utilized for their convenience and their genetic similarity to humans. As mammals, rodents share similar biological processes and systems to their human counterparts and, therefore, are an effective indicator as to the likelihood of success associated with a proposed medical procedure.

In many surgical environments, a surgical table or apparatus is utilized to support and secure the subject during a procedure. A surgical table may secure a specimen at a desired position and may limit motion of the specimen to ensure that the procedure is completed properly. Additionally, anesthesia is also often utilized to ensure that the specimen remains in a desired position. Traditionally, a separate anesthetic supply device (e.g., free standing) is utilized to deliver an anesthetic to the specimen resulting in various tubes and cords freely hanging to connect the anesthetic supply device to the specimen. In these circumstances, navigation around the specimen during operation is tedious and creates the risk of disturbing the specimen. Additionally, repositioning of the specimen during a procedure, using conventional technologies, requires releasing the specimen from the surgical table and/or moving the physician about the surgical table.

Embodiments of the present invention that are described hereinbelow provide a rotatable surgical table for processing a specimen. In addition, embodiments of the present invention also provide for supplying an anesthetic to the specimen via the surgical table, as opposed to a separate device, such that the specimen may receive continuous anesthetic during rotation of the surgical table. In addition to rodents and small animals, one of ordinary skill in the art will appreciate that the devices and methods discussed herein may be scaled to accommodate any patient or specimen.

For the sake of clarity and convenience of description, the embodiments that are described herein are made in reference to various components, elements, members, or the like that allow and/or maintain fluid communication. As used herein, the term "fluid" may refer to a substance, such as a liquid or gas, which does not have a fixed shape and is capable of flowing. By way of example, in some embodiments described below, a gaseous anesthetic may be considered a fluid, and may be administered to a specimen via various respective channels in fluid communication with one another (e.g., an anesthetic supplied to a first base channel in fluid communication with a first platform channel).

Rotatable Surgical Table

Some embodiments described herein include a base member and platform member. The base member and the platform member may abut one another and be configured such that the platform member may rotate relative to the base member. The platform member and base member may each define one or more channels where the one or more channels of the platform member are in fluid communication with the one or more channels of the base member. In some embodiments, the platform member and the base member may each define two channels. In such an embodiment, a treatment agent (e.g., an anesthetic) may be supplied to a first channel of the base member that is in fluid communication with a first channel of the platform member. In some embodiments, a nozzle (such as, for example, a nose cone) may be affixed to the top surface of the platform member such that a specimen (e.g., a mouse of other rodent) secured to the platform may be administered an anesthetic. This nozzle may be in fluid communication with the first channel of the platform member. As described in further detail below, some embodiments of the rotatable surgical table may utilize the second channels of both the platform member and the base member in conjunction with a reverse flow (e.g., vacuum suction) to create a self-scavenging system at the nozzle.

With reference to FIG. 1, an opaque top view of the base member 100 is shown with a first surface 105, gasket 110, a first base channel 120, a second base channel 130, an inner annular chamber 115, an outer annular chamber 135, a first side port 125, and a second side port 140. The first surface 105 of the base member 100 may be configured to abut the bottom surface of a platform member (e.g., bottom surface 500 in FIG. 5). In some embodiments, the base member may define one or more annular walls. These annular walls may define one or more annular chambers. In the example embodiment shown in FIG. 1, an inner annular chamber 115 and an outer annular chamber 135 are created by annular walls 145, 150 defined by the first surface 105 of the base member 100. In order to promote sealing of the annular chambers and base channels from the environment, one or more gaskets 110 may be disposed on the first surface 105 of the base member 100.

The base member 100 may further define one or more channels to deliver a fluid from an external source coupled with one or more side ports 125, 140 to the respective inner annular chamber 115 or outer annular chamber 135, or to remove fluid from the inner annular chamber 115 or outer annular chamber 135 via a respective one or more side ports 125, 140. By way of example, the base member 100 shown in FIG. 1 defines a first base channel 120 and a second base channel 130. As shown in FIG. 1, these channels may be located between a top surface (e.g., first surface 105) and a bottom surface (e.g., bottom surface 200 shown in FIG. 1) of the base member 100. The base member 100 may be a solid body such that the first base channel 120 and the second base channel 130 are enclosed in and formed by the body of the base member 100. In some embodiments, the channels 120, 130 may be formed in or on the base member 100 or may include one or more separately-attached conduits. These channels may be configured such that a fluid may travel therethrough. In some embodiments, the base member 100 may be integrated into a larger table or work surface such that the top surface of the base member is part of the larger table or work surface.

In some embodiments, the base member 100 may define one or more side ports (e.g., first side port 125 and second side port 140). The first base channel 120 may be in fluid communication with a first side port 125. In some embodiments, this first side port 125 may be supplied with a fluid, such as an anesthetic or other treatment agent, that flows from the first side port 125 through the first base channel 120. The second base channel 130 may be in fluid communication with a second side port 140. In some embodiments, a reverse flow (e.g., vacuum or other suction) may be applied to the second side port 140 such that a fluid may travel through the second base channel 130. In some embodiments, the second base channel 130 may receive the fluid (e.g., anesthetic or other treatment agent) from the second side port 140, while the first base channel 120 receives the reverse flow. In some other embodiments, both of the channels 120, 130 may receive the fluid or reverse flow, either simultaneously or alternately, as required.

With reference to FIG. 2, a bottom view of the base member 100 is depicted showing a second, bottom surface 200 and the respective channels 120, 130 therein. As shown in FIG. 2, the first base channel 120 may be positioned so as to connect the first side port 125 and the inner annular chamber 115. Similarly, the second base channel 130 may be positioned so as to connect the second side port 140 and the outer annular chamber 135. As shown in FIG. 2, in some embodiments, excess material may be removed from the base member 100, such as shown in FIG. 2, to reduce weight and cost of manufacturing (e.g., partially hollowed out). As discussed above, in some embodiments, the base member 100 may be a solid member such that the first channel 120 and the second base channel 130 are disposed between the first surface 105 and the second surface 200 of the base member 100 (i.e., located between the top and bottom of the base member). In some embodiments, excess material may be removed from the base member 100, such as shown in FIG. 2, to reduce weight and cost of manufacturing.

With reference to FIG. 3, a top view of the base member 100 of FIG. 1 is illustrated with the channels 120, 130. Here, the first surface 105 of the base member 100 clearly shows the arrangement of the first base channel 120 and the second base channel 130. These channels are shown terminating at the inner annular chamber 115 and the outer annular chamber 135, respectively. In addition, the gaskets 110 are shown atop the first surface 105. The gaskets 110 may be disposed on a top edge of the one or more annular walls 145, 150 and may be configured to encircle one or more annular walls defined by a platform member (e.g., annular walls 505, 510 of platform member 400 in FIG. 5). The gaskets 110 may be further configured to extend radially inward beyond their respective annular wall to prevent air leakage between chambers and channels. For example, a gasket 110 disposed atop of outer annular wall 150 of the base member 100 may extend radially inward such that the gasket 110 contacts the outer annular wall 505 of the platform member 400, hereinafter described. In such an example, the gasket 110 may substantially seal the outer annular chamber about a linear contact which encircles the outer annular wall 505. The gaskets 110 may further be configured to be recessed into the bottom surface of the base member 105 such that the gaskets 110 of the base member 100 do not contact the bottom surface 500 of the platform member 400 when the base member 100 and platform member 400 abut.

With reference to FIG. 4, a top view of a platform member 400 is illustrated installed on a base member 100. The depicted platform member 400 includes a top surface 405, a nozzle 410, one or more notches 415, and a nozzle channel 425. The platform 400 is configured to hold the specimen thereon and rotate relative to the base member 100. By way of example, the platform 400 may rotate 360 degrees relative to the base member 100 in either direction (e.g., a clockwise and/or counter-clockwise rotation). Further, the present disclosure contemplates that any number of full or partial rotations of the platform 400 may be made relative to the base member 100, in either direction. The nozzle 410 may supply a treatment agent to the specimen as discussed herein. As described in greater detail below, with regards to FIG. 6, the platform member may define one or more platform channels (e.g., first platform channel 515 and second platform channel 520).

Similarly, with reference to FIG. 5, a bottom view of an embodiment of the platform member 400 is illustrated. The depicted platform member 400 includes a bottom surface 500, an inner annular wall 510, and outer annular wall 505, a first platform channel 515, a second platform channel 520, and one or more notches 415. In some embodiments, at least a portion of the bottom surface 500 of the platform member 400 may be configured to abut the first surface 105 of the base member 100 during operation. In some embodiments, the bottom surface 500 may define an inner annular wall 510 and an outer annular wall 505. The base member 100 may be configured to receive the platform member such that the inner annular wall 510 and the outer annular wall 505 nest in spaced defined by the one or more annular walls 145, 150 defined by the first surface 105 of the base member 100. By way of example, when the first surface 105 of the base member 100 abuts the bottom surface 500 of the platform member 400, the outer annular wall 150 of the base member 100 may encircle the outer annular wall 505 of the platform member 400. Likewise, in such an example, the inner annular wall 145 of the base member 100 may encircle the inner annular wall 510 of the platform member 400. Further, in such an embodiment, the connection between the platform member 400 and the base member 100 may be such that the inner annular chamber 115 is defined radially inward of the inner annular wall 510, and the outer annular chamber 135 is defined between the inner annular wall 510 and the outer annular wall 505.

In some embodiments, only one of the base member 100 and the platform member 400 may define annular walls and/or chambers. In other embodiments, the base member 100 and/or the platform member 400 may be configured to receive one or more annular walls unattached to either member. For example, one or more separate wall members may be placed between the platform member and base member to create one or more chambers. Additionally, although shown as circular or annular walls, the present disclosure contemplates that any shape capable of creating a rotatable enclosure or chamber may be used.

With further reference to FIG. 5, one end of the first platform channel 515 may terminate in the inner annular chamber 115 located in the space created radially inward of the inner annular wall 510. Similarly, one end of the second platform channel 520 may terminate in the outer annular chamber 135 located in the space created between the inner annular wall 510 and the outer annular wall 505. The connection between the base member 100 and the platform member 400 may be such that the inner annular chamber 115 and the outer annular chamber 135 may be enclosed and may substantially airtight from one another. The connection between the base member 100 and the platform member 400 may be such that the first platform channel 515 and the first base channel 120 may be in continuous fluid communication. Similarly, the connection between the base member 100 and the platform member 400 may also be such that the second platform channel 520 and the second base channel 130 may be in continuous fluid communication. By way of example, a fluid supplied to the first side port 125 may flow through the first base channel 120, into the inner annular chamber 115, and through the first platform channel 515.

In some embodiments, the connection between the base member 100 and the platform member 400 may be such that the platform member 400 may rotate about the base member. In some embodiments, the platform member 400 and base member 100 may allow unlimited rotation therebetween. The rotation of the platform member 400 about the base member 100 may maintain continuous fluid communication between the first base channel 120 and the first platform channel 515, as well as continuous fluid communication between the second base channel 130 and the second platform channel 520 for any rotational position of the platform member relative to the base member. As discussed above, one or more gaskets 110 may facilitate this connection between the base member 100 and the platform member 400 and help to prevent leakage of fluids supplied to the apparatus. Additionally, the platform member 400 may define one or more notches 415 along the edge of the platform member 400 such as to facilitate user rotation of the platform member 400 about the base member 100.

With reference to FIG. 6, a bottom view of the platform member 400 is illustrated showing the platform channels 515, 520. As discussed above, the first platform channel 515 is shown terminating on one end radially inward of the inner annular wall 510 and the second platform member 520 is show terminating on one end between the inner annular wall 510 and the outer annular wall 505. The ends of the first platform channel 515 and the second platform channel 520 opposite the annular chambers may each terminate at the top surface 405 of the platform member 400. As shown in FIG. 4, in some embodiments, the one or more platform channels may be in fluid communication with a nozzle channel 425. As shown in FIGS. 5-6, these channels may be located between a top surface 405 and a bottom surface 500 of the platform member 400. In some embodiments, the platform member 400 may be solid such that the first platform channel 515 and the second platform channel 520 are enclosed in the body of the platform member 400.

With reference to FIG. 7, an example nozzle 410 is illustrated affixed atop the top surface 405 of the platform member 400. The nozzle 410 may include a nozzle channel 425, an inner shell 705, an outer shell 710, and a shell channel 715. In the example embodiment shown in FIG. 7, the nozzle channel 425 may be in fluid communication with the first platform channel 515 and may extend through the outer shell 710 and inner shell 705, terminating within the inner shell 705 of the nozzle 410. Additionally, a shell channel 715 may be defined by the space located between the inner shell 705 and the outer shell 710. In some still further embodiments, the shell channel 715 may be in fluid communication with the second platform channel 520. The shell channel 715 may terminate about a peripheral edge of the nozzle 410, such that a semi-circular opening is defined between the inner shell 705 and the outer shell 710 as shown in FIG. 7. In some embodiments, an anesthetic may be administered to a subject using the nozzle channel 425, and a reverse flow (e.g., vacuum or other suction) may be applied to the shell channel 715 around the nozzle channel 425 to create a self-scavenging system whereby fluid is released within the nozzle 410 at an interior of the inner shell 705, and the fluid may be drawn into the shell channel 715 between the inner shell 705 and outer shell 710 at the peripheral edge. The specimen's head may be positioned in the nozzle 410 internal of the inner shell 705 to receive the fluid treatment agent. Although the example embodiment of FIG. 7 illustrates the nozzle 410 affixed to the top surface 405 of the platform member 400, the present disclosure contemplates that the nozzle 410 may be located anywhere in proximity to the platform member so long as fluid communication between the nozzle channel 425 and the first platform channel 515 is maintained.

With reference to FIGS. 8-9, cross-sectional views of the base member 100 and the platform member 400 are illustrated. In FIG. 8, the first base channel 120 is illustrated terminating in the first annular chamber 115 in the space radially inward of (bounded by) the inner annular wall 145 defined by the first surface 105 of the base member 100. The second base channel 130 is illustrated terminating in the outer annular chamber 135 in the space created between the inner annular wall 145 and the outer annular wall 150. Gaskets 110 are illustrated atop each of the inner annular wall 145 and the outer annular wall 150. In some embodiments, as previously described, the gaskets may extend radially inward beyond their respective annular wall to prevent air leakage between chambers and channels.

With reference to FIG. 9, a cross-sectional view of the base member 100 and the platform member 400 are shown together. In FIG. 9, the first platform channel 515 is illustrated terminating on one end in the inner annular chamber 115 in the space radially inward of the inner annular wall 510. The first platform channel 515 is illustrated terminating on a second end at a position on the top surface 405 in fluid communication with a nozzle channel 425. As discussed above, the nozzle channel 425 may be in fluid communication with the first platform channel 515 and may extend through the outer shell 710 and inner shell 705, terminating within the inner shell 705 of the nozzle 410. The second platform channel 520 is illustrated terminating on one end in the outer annular chamber 135 in the space created between the inner annular wall 510 and the outer annular wall 505. The second platform channel 520 is illustrated terminating on a second end at a position on the top surface 405 in fluid communication with a shell channel 715. As discussed above, the shell channel 715 may be in fluid communication with the second platform channel 520 and may terminate about a peripheral edge of the nozzle 410, such that a semi-circular opening is defined between the inner shell 705 and the outer shell 710 as shown in FIG. 7.

With reference to FIG. 10, a perspective view of a rotatable surgical table is displayed with the first surface 105 of base member 100 abutting the bottom surface of the platform member 400 (e.g., bottom surface 500 shown in FIG. 5). As discussed further below, a user may rotate the platform member 400 relative to the base member 100 through use of the one or more notches 415.

With reference to FIG. 11, a bottom view of an alternative platform member 400 is displayed. In FIG. 11, two electrical contacts 1100 are illustrated disposed on the bottom surface 500 of the platform member 400. In some embodiments, the rotatable surgical table may comprise a heated surface (e.g., heated surface 1205 in FIG. 12) disposed on the top surface of the platform member (e.g., top surface 405 in FIG. 12). The electrical contacts 1100 may correspond to ends of a transmission medium (e.g., wire, coil, or the like) disposed within the body of the platform member 400 and configured to transmit an electrical current. In some embodiments, the base member 100 may also comprise a transmission medium configured to transmit an electrical current. In such an embodiment, the electrical contacts 1100 may be in electrical communication with the transmission medium of the base member when the bottom surface 500 platform member 400 abuts the first surface 105 of the base member 100. Electrical communication may further be maintained when the platform member 400 is rotated about the base member 100 via electric brushes, slip rings, rotary electrical interfaces, rotating electrical connectors, collectors, swivels, electrical rotary joints, rotary unions, or the like disposed between the platform member 400 and the base member 100. In some embodiments, the platform member 400 and/or base member 100 may be configured to be in electrical communication with a power source (e.g., battery, power outlet, or the like) such that an electrical current may be provided to the transmission medium.

With reference to FIG. 12, a top view of an alternative platform member 400 is illustrated in conjunction with a base member (e.g., base member 100 of FIG. 1). In some embodiments, the platform member 400 may further comprise a heated surface 1205. As described above, the heated surface 1205 may define a pad configured to receive a specimen. The heated surface 1205 may, via an electrical current supplied by the transmission medium associated with the electrical contacts 1100, generate heat (e.g., via resistors or the like) such that the body temperature of the specimen may be influenced. In some embodiments, the heated surface 1205 (as seen in FIG. 13) may extend into an area covered by the nozzle 410. The present disclosure contemplates that the heated surface 1205 may cover any portion of the top surface 405 of the platform member 400, and/or that heat may be applied to any member or surface of any embodiment discussed herein. Although described in conjunction with an electrically powered heating pad, the present disclosure contemplates that heat may be provided to the specimen from a variety of means (e.g., chemical heat pad, heating lamp, or the like).

With continued reference to FIG. 12, the platform member 400 may further define one or more openings 1210 configured to receive one or more corresponding posts 1215. The one or more openings 1210 may be positioned at any location upon the top surface 405 of the platform member 400. Further, the one or more openings 1210 may be of any depth required to secure the location of an object disposed inside the one or more openings 1210 (e.g., post 1215). As seen in the enlarged area depicting post 1215, the one or more posts 1215 may be stepped (e.g., diameters of varying size) such that only a portion of the post 1215 may be disposed within the body of the platform member 400 when the post 1215 is received by an opening 1210.

In some embodiments, the posts 1215 may be configured such that a securing member (e.g., string, elastic band, or the like) may wrap around the post and specimen in order to secure the specimen to the platform member 400. In some other embodiments, the posts 1215 may be positioned such that they form a boundary. By way of example, the one or more posts 1215 may be disposed about the perimeter of the heated surface 1205 in order to limit or otherwise restrict the movement of a specimen disposed on the heated surface. In some still further embodiments, the top surface 405 of the platform member 400 may comprise a rubberized surface at least partially covering the surface of the platform member 400. By way of example, the rubberized surface may define a layer of an elastomer (e.g., rubber or the like) of 3 mm-4 mm in thickness such that a specimen disposed on the rubberized surface may be pinned to the rubberized surface. Additionally, the rubberized surface may also facilitate positioning of a specimen disposed thereon via the friction between the specimen and rubberized surface resisting the movement of the specimen during possible rotation of the platform member 400.

With reference to FIGS. 12-13, an alternative nozzle 410 (e.g., nose cone) for use in some embodiments is illustrated. The nozzle 410, with reference to FIG. 13, may comprise an inner shell 705, an outer shell 710, and a shell channel 715. Similar to the nozzle 410 in FIG. 7, described above, the shell channel 715 may be defined by the space created between the outer shell 710 and inner shell 705, and may terminate about a peripheral edge of the nozzle 410. Additionally, the shell channel 715 may be in fluid communication with the second platform channel 520, and may be configured in some embodiments, in conjunction with a reverse flow (e.g., vacuum suction) applied to the rotatable table (via side port 140 discussed above), to create a self-scavenging system.

Additionally, in some embodiments as seen in FIG. 13, the nozzle 410 may be configured without a nozzle channel 425 (as seen in FIG. 4) affixed to the top surface 405 of the platform member 400. In such an embodiment, the nozzle 410 may be configured such that the first platform channel 515 terminates at a point disposed on the top surface 405 of the platform member 400. The nozzle 410 may further be configured to cover the first platform channel 515 in order to direct the fluid flow supplied by the first platform channel 515.

With reference to FIGS. 14-15, in some embodiments, an alternative platform member may be provided that is comprised of two separable members, a top platform member 1400 and a bottom platform member 1500. As seen in FIG. 14, the top platform member 1400 may define a first top platform opening 1410, a second top platform opening 1405, a bottom surface 1420, a recessed surface 1425, and a first keying feature 1415. The top platform member 1400 may also be configured to receive a bottom platform member (e.g., bottom platform member 1500 in FIG. 15). By way of example, the top platform member may define a recess configured to receive the bottom platform member 1500 such that the top surface of the bottom platform member (e.g., top surface 1505 in FIG. 15) abuts the recessed surface 1425 of the top platform member 1400. In some embodiments, the thickness of the top platform member (i.e., the difference between the surface to which the specimen is secured and the recessed surface 1425) may be between 1-3 mm.

In some embodiments, the top platform member 1400 may be configured such that the first top platform opening 1410 is in fluid communication with the first platform channel 515. Additionally, the top platform member 100 may be configured such that the second top platform opening 1405 is in fluid communication with the second platform channel 520. In some embodiments, as above, the first top platform opening 1410 may be configured to administer an anesthetic to a rodent via a nozzle disposed on the top surface of the top platform member 1400 (e.g., nozzle 410). Additionally, as above, the second top platform opening 1405 may be in fluid communication with the second platform channel 520 and configured to provide a reverse suction (e.g. a vacuum suction). This communication may create a self-scavenging system via a channel in fluid communication with the second top platform opening 1405 disposed about the peripheral edge of a nozzle disposed on the top surface of the top platform member (e.g., shell channel 715 in FIG. 12). The top platform member 1400 may further define a bottom surface 1420 configured to abut a top surface of a base member (e.g., first surface 105 of the base member 100 in FIG. 1).

With reference to FIG. 15, a bottom platform member 1500 is illustrated with a top surface 1505, a bottom surface 1510, a first platform channel 515, a second platform channel 520, a heated surface 1205, electrical elements 1520, and second keying feature 1515. As discussed with reference to FIG. 14, the bottom platform member 1500 may be configured to be received by the top platform member 1400. By way of example, the bottom platform member 1500 may nest within the top platform member 1400 such that the top surface 1505 abuts the recessed surface 1425. In such an example, the bottom surface 1510 of the bottom platform member 1500 may be substantially level with the bottom surface 1420 of the top platform member 1400 such that both the bottom surfaces 1420, 1510 abut the top surface of a base member, when the separable platform member (e.g., bottom platform member 1500 and top platform member 1400) is received by the base member (e.g., base member 100 in FIG. 1).

With continued reference to FIG. 15, in some embodiments, the bottom platform member 1500 may comprise a heated surface 1205. The heated surface 1205 may, via an electrical current supplied by the transmission medium associated with the electrical contacts electrical elements 1520, generate heat (e.g., via resistors or the like) such that the body temperature of a specimen affixed to a top surface of the top platform member 1400 may be influenced. By way of example, when the bottom platform member 1500 is received by the top platform member 1400, the heated surface 1205 may heat (e.g., via conduction, convection, or the like) the top platform member 1400. The present disclosure contemplates that the heated surface 1205 may cover any portion of the top surface 1505 of the bottom platform member 1500, and/or that heat may be applied to any member or surface of any embodiment discussed herein. As above, although described in conjunction with an electrically powered heating pad, the present disclosure contemplates that heat may be provided to a specimen from a variety of means (e.g., chemical heat pad, heating lamp, or the like).

In some embodiments, the top surface 1505 may further comprise electrical elements 1520. The electrical elements 1520 may correspond to a transmission medium (e.g., wire, coil, or the like) disposed within the body of the bottom platform member 1500 and configured to transmit an electrical current. As above, in some embodiments, a base member (e.g., base member 100 in FIG. 1) may also comprise a transmission medium configured to transmit an electrical current. In such an embodiment, the electrical elements 1520 may further include electrical contacts (e.g., electrical contacts 1100 in FIG. 11) disposed on the bottom surface 1510 of the bottom platform member 1500. The electrical elements 1520 may be in electrical communication with a transmission medium of the base member when the bottom surface 1510 bottom platform member 1500 abuts the first surface 105 of the base member 100. Electrical communication may further be maintained when the separable platform member (e.g., bottom platform member 1500 and top platform member 1400) is rotated about a base member via electric brushes, slip rings, rotary electrical interfaces, rotating electrical connectors, collectors, swivels, electrical rotary joints, rotary unions, or the like disposed between the separable platform member and the base member. In some embodiments, the bottom platform member 1500 and/or base member may be configured to be in electrical communication with a power source (e.g., battery, power outlet, or the like) such that an electrical current may be provided to the transmission medium.

With continued reference to FIGS. 14-15, the top platform member 1400 and the bottom platform member 1500 may further define a first keying element 1415 and a second keying element 1515, respectively. These keying elements may be configured such that the top platform member 1400 may only receive the bottom platform member 1500 in a defined orientation. By way of example, the first keying element 1415 may define a 9-sided polygon and the second keying element 1515 may define a corresponding 9-side polygon. In such an example, the keying elements may be configured to assist the top platform member 1400 receiving the bottom platform member 1500 in an orientation such that the first top platform opening 1410 and second top platform opening 1405 may be in fluid communication with the first platform channel 515 and second platform channel 520, respectively. Although illustrated in FIGS. 14-15 as a 9-side polygon, the present disclosure contemplates that the first keying element 1415 and the second keying element 1515 may define any number of shapes without limitation. In some embodiments, the first keying element 1415 and second keying element 1515 may each define corresponding unique shapes such that the top platform member 1400 may only receive the bottom platform member 1500 in an orientation in which fluid communication is maintained between the bottom platform member 1500 and the top platform member 1400. In such an embodiment, the unique shapes, defined by the keying elements, may function to prevent any incorrect meshing between the platform members and prevent leakage of any gas traveling therein.

The present disclosure also contemplates that the top platform member 1400 may be created from any suitable autoclavable material known in the art (e.g., polypropylene, stainless steel, or the like). By way of example, the top platform member 1400 may be comprised of a polypropylene plastic such that the top platform member (i.e., the surface contacting the specimen) may be removed following a procedure, and sterilized via an autoclave procedure. The present disclosure further contemplates that the bottom platform member 1500 may be created from a soft rubber material to facilitate rotation of the bottom platform member 1500 relative to a base member.

Example Operation and Method

As will be appreciated by the description above, the rotatable surgical table, systems, and methods described herein may be used to process (e.g., treat, operate on, dissect, etc.) a specimen (e.g., a rat or other rodent or small animal). In an example embodiment shown in FIGS. 1-7, a specimen may be affixed to the top surface 405 of the platform member 400. The first side port 125 of the base member 100 may be supplied with an anesthetic or other treatment agent. This first side port 125 may be connected to a supply (e.g., storage tank) via one or more connectors (e.g., medical tubes) that engage the first side port. The first side port 125 may be in fluid communication with the first base channel 120, located in the base member 100, such that the anesthetic flows from the anesthetic supply, through the connector and into the first base channel 120 via the first side port 125. The base member 100 may be configured to receive and/or otherwise connect with the rotatable platform member 400. At least one of the base member 100 and the base member 400 may define one or more annular walls. The connection between the base member 100 and the platform member 400 may be such that the platform member 400 abuts (e.g., rests atop) the base member 100. In the example embodiment, the annular walls 505 510 of the platform member 400 nest within the base member 100.

In the example embodiment, the connection between the base member and the platform member further defines an inner annular chamber 115 and an outer annular chamber 135. The inner annular chamber 115 may be in fluid communication with the first base channel 120. The platform member 400 may further define a first platform channel 515 in fluid communication with the inner annular chamber 115, and in fluid communication with the first base channel 120. Therefore, the treatment agent may flow from the first base channel 120 through the first platform channel 515 via the inner annular chamber 115. In the example embodiment, the first platform channel 515 may terminate at a position on the top surface 405 of the platform member. Further, this first platform channel 515 may be in fluid communication with a nozzle channel 425. This nozzle channel 425 may receive the treatment agent (e.g., a gaseous anesthetic) flowing from the first platform channel 515 and dispose of the anesthetic to a specimen via the nozzle 410.

Similarly, the second side port 140 of the base member 100 may be supplied with a reverse flow (e.g., vacuum or other suction). This second side port 140 may be connected to a supply (e.g., storage tank) via one or more connectors (e.g., medical tubes). The second side port 140 may be in fluid communication with the second base channel 130, located in or attached to the base member 100, such that a reverse flow removes fluid from the second base channel 130 via the second side port 140. As discussed above, the base member 100 may be configured to receive and/or otherwise connect with the platform member 400 and may define one or more annular walls.

In the example embodiment, the connection between the base member and the platform member defines an outer annular chamber 135. The outer annular chamber 135 may be in fluid communication with the second base channel 130. The platform member 400 may further define a second platform channel 520 in fluid communication with the outer annular chamber 135, and inherently in fluid communication with the second base channel 130. Therefore, the reverse flow may draw fluid from the second platform channel 520 to the second base channel 130 via the outer annular chamber 135 and out the side port 140. In the example embodiment, the second platform channel 520 may terminate at a position on the top surface 405 of the platform member. Further, this second platform channel 520 may be in fluid communication with a shell channel 715 between the inner shell 705 and the outer shell 710. This shell channel 715 may be disposed around the edge of the nozzle 410 and may be in fluid communication with the second platform channel 520. Accordingly, a reverse flow may be applied to the shell channel 715 via the second platform channel 520. The reverse flow or suction applied at the shell channel 715 around the nozzle 410 and nozzle channel 425 may create a self-scavenging system. As would be appreciated by one of ordinary skill in the art in light of the present disclosure, the self-scavenging system may be reversed, such that the treatment agent is released from the shell channel 715 and excess agent is drawn into the nozzle channel 425 by the reverse flow.

The example method of processing a specimen using the rotatable surgical table includes supplying an anesthetic via the first side port 125 through the first base channel 120, the inner annular chamber 115, the first platform channel 515, and the nozzle channel 425, and is administered to the specimen. A reverse flow (e.g., a pump or suction) may be applied to the second side port 140 such that the air or fluid located about the shell channel 715 enters the shell channel 715, flows through the second platform channel 520, the outer annular chamber 135, the second base channel 130, and to a reverse flow supply (e.g., a pump) via the second side port 140.

Additionally, during processing of a specimen, the above described connection between the platform member 400 and the base member 100 is configured to allow the platform member 400 to be rotated about the base member 100 while maintaining continuous fluid communication between the above described channels at any angle and for any number of rotations. The annular chambers may be arranged concentrically, such that each annular chamber is positioned a predetermined radial distance from the rotational center of the platform/base interface. Such an arrangement may facilitate the unlimited rotational connectivity of the embodiments described herein. One or more gaskets may be located between the base member 100 and platform member 400 to facilitate maintaining fluid communication and prevent air leakage at the interface between the platform 400 and the base 100. Further, the platform member 400 may be notched (e.g., notches 415) to assist the user in effectuating the rotation of the platform member 400 about the base member 100.

The present disclosure contemplates that the present invention may be created from any suitable material known in the art (e.g., plastic, resin, ceramic, metal, rubber, or the like). By way of example, the present invention may be created through 3-D printing, injection molding, among others without limitation. Additionally, due to the oft required sterile nature of medical environments, the present disclosure contemplates that the present invention may be comprised of bacterial resistant materials or subjected to any manner of sterilization procedure or device (e.g., an autoclave). Although the present invention is depicted as two members (e.g., a base member and a platform member with an attached nozzle), the present disclosure contemplates that the present invention may be comprised of any number of individual members or pieces so long as continuous fluid communication is maintained between the respective channels.

In embodiments discussed herein, a treatment agent is provided through one or more of the channels to the nozzle. In some embodiments, the treatment agent may be an anesthetic, such as, for example, vaporized isoflurane.

Many modifications and other embodiments of the inventions set forth herein will come to mind to one skilled in the art to which these inventions pertain having the benefit of the teachings presented in the foregoing descriptions and the associated drawings. For example, the base member and platform member shown and described herein each include two channels, which in some embodiments may respectively supply a treatment agent and apply a reverse flow to the nozzle. In some embodiments, only one channel may be provided that supplies a treatment agent or applies a reverse flow. In some other embodiments, three or more channels may be provided to apply multiple treatment agents, multiple reverse flows, or combinations thereof. In instances having three or more channels, three or more annular chambers may be likewise arranged in concentric positions in a similar manner to the embodiments shown in FIGS. 1-7. Although the figures only show certain components of the apparatus, systems, and associated methods described herein, it is understood that various other components may also be part of the rotatable surgical table. In addition, the methods described above may include fewer steps in some cases, while in other cases may include additional steps.

Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A nozzle on a surgical table, the nozzle comprising:
an inner shell affixed to a top surface of the surgical table, wherein the inner shell defines a nozzle interior, and wherein the nozzle interior defines a nozzle channel; and
an outer shell affixed to the top surface of the surgical table to define a nozzle shell channel between the inner shell and the outer shell; and
wherein:
the nozzle channel is in fluid communication with a first channel extending through the top surface of the surgical table and defined at least partially within an interior of the surgical table;
the nozzle shell channel is in fluid communication with a second channel extending through the top surface of the surgical table and defined at least partially within the interior of the surgical table.

2. The nozzle of claim 1, wherein:
the first channel is in fluid communication with a treatment agent supply configured to supply treatment agent through the first channel to the nozzle channel; and
the second channel is in fluid communication with a vacuum system to scavenge gas from the nozzle interior through the nozzle shell channel.

3. The nozzle of claim 1, wherein:
the second channel is in fluid communication with a treatment agent supply configured to supply treatment agent through the second channel to the nozzle shell channel; and
the first channel is in fluid communication with a vacuum system to scavenge gas from the nozzle interior through the nozzle channel.

4. The nozzle of claim 1, wherein the nozzle defines a nose cone on the top surface of the surgical table, and wherein:
the inner shell defines an interior surface of the nose cone between a closed end and a semi-circular open end of the inner shell, and wherein the nozzle channel terminates at a nozzle channel opening defined within the closed end of the inner shell; and
at least a portion of the outer shell is spaced apart from at least a portion of the inner shell to define the nozzle shell channel and wherein the outer shell defines an exterior surface of the nose cone between a closed end and a semi-circular open end of the outer shell.

5. The nozzle of claim 4, wherein the nozzle shell channel terminates at a nozzle shell channel opening between a terminal edge of the inner shell at the semi-circular open end of the inner shell and a portion of the outer shell.

6. The nozzle of claim 5, wherein the nozzle shell channel opening has a semi-circular shape contoured with the semi-circular open end of the inner shell.

7. The nozzle of claim 1, wherein the nozzle defines a nose cone on the top surface of the surgical table, and wherein:

the inner shell defines an interior surface of the nose cone between a closed end and a semi-circular open end of the inner shell;

at least a portion of the outer shell is spaced apart from at least a portion of the inner shell to define the nozzle shell channel and wherein the outer shell defines an exterior surface of the nose cone between a closed end and a semi-circular open end of the outer shell; and the nozzle channel terminates at a nozzle channel opening defined within the top surface of the surgical table, wherein the nozzle channel opening is positioned within the nozzle interior.

8. A surgical table comprising:

a base member defining a first base channel and a second base channel;

a platform member in rotational contact with the base member, wherein the platform member defines:
   a top surface and a bottom surface, wherein the bottom surface is configured to abut the base member;
   a first platform channel in fluid communication with the first base channel; and
   a second platform channel in fluid communication with the second base channel; and a nozzle comprising:
   an inner shell affixed to the top surface of the platform member, wherein the inner shell defines a nozzle interior, and wherein the nozzle interior defines a nozzle channel; and
   an outer shell affixed to the top surface of the platform member to define a nozzle shell channel between the inner shell and the outer shell.

9. The surgical table of claim 8, wherein:
the nozzle channel is in fluid communication with the first platform channel; and
the nozzle shell channel is in fluid communication with the second platform channel.

10. The surgical table of claim 9, wherein:
the first base channel is in fluid communication with a treatment agent supply configured to supply treatment agent through the first base channel and the first platform channel to the nozzle channel; and
the second base channel is in fluid communication with a vacuum system to scavenge gas from the nozzle shell channel through the second platform channel and the second base channel.

11. The surgical table of claim 9, wherein:
the second base channel is in fluid communication with a treatment agent supply configured to supply treatment agent through the second base channel and the second platform channel to the nozzle shell channel; and
the first base channel is in fluid communication with a vacuum system to scavenge gas from the nozzle channel through the first platform channel and the first base channel.

12. The surgical table of claim 8, wherein the nozzle defines a nose cone on the top surface of the platform member, and wherein:
the inner shell defines an interior surface of the nose cone between a closed end and a semi-circular open end of the inner shell, and wherein the nozzle channel terminates at a nozzle channel opening defined within the closed end of the inner shell; and
at least a portion of the outer shell is spaced apart from at least a portion of the inner shell to define the nozzle shell channel and wherein the outer shell defines an exterior surface of the nose cone between a closed end and a semi-circular open end of the outer shell.

13. The surgical table of claim 12, wherein the nozzle shell channel terminates at a nozzle shell channel opening between a terminal edge of the inner shell at the semi-circular open end of the inner shell and a portion of the outer shell.

14. The surgical table of claim 13, wherein the nozzle shell channel opening has a semicircular shape contoured with the semi-circular open end of the inner shell.

15. The surgical table of claim 8, wherein the nozzle defines a nose cone on the top surface of the platform member, and wherein:
the inner shell defines an interior surface of the nose cone between a closed end and a semi-circular open end of the inner shell;
at least a portion of the outer shell is spaced apart from at least a portion of the inner shell to define the nozzle shell channel and wherein the outer shell defines an exterior surface of the nose cone between a closed end and a semi-circular open end of the outer shell; and
the nozzle channel terminates at a nozzle channel opening defined within the top surface of the platform member, wherein the nozzle channel opening is positioned within the nozzle interior.

16. A method comprising:
providing a nozzle affixed to a top surface of a surgical table, wherein the nozzle comprises:
   an inner shell affixed to the top surface of the surgical table, wherein the inner shell defines a nozzle interior, and wherein the nozzle interior defines a nozzle channel in fluid communication with a first channel extending through the top surface of the surgical table and defined within an interior of the surgical table; and
   an outer shell affixed to the top surface of the surgical table to define a nozzle shell channel between the inner shell and the outer shell, and wherein the nozzle shell channel is in fluid communication with a second channel extending through the top surface of the surgical table and defined within the interior of the surgical table; and
circulating a treatment agent through the first channel, the second channel, and the nozzle interior.

17. The method of claim 16, wherein circulating a treatment agent through the first channel, the second channel, and the nozzle interior comprises:
providing the treatment agent to the nozzle interior via the nozzle channel and the first channel; and
scavenging at least a portion of the treatment agent provided to the nozzle interior via the nozzle shell channel and the second channel.

18. The method of claim 16, wherein circulating a treatment agent through the first channel, the second channel, and the nozzle interior comprises:
providing the treatment agent to the nozzle interior via the nozzle shell channel and the second channel; and
scavenging at least a portion of the treatment agent provided to the nozzle interior via the nozzle channel and the first channel.

19. The method of claim 16, wherein the surgical table comprises:
a base member; and
a platform member in rotational contact with the base member, wherein the platform member defines a top surface and wherein the top surface of the surgical table is embodied as the top surface of the platform member;
wherein the first channel comprises a first base channel extending through the base member and a first platform channel extending through the platform member, wherein the first platform channel is in fluid communication with the first base channel;

wherein the second channel comprises a second base channel extending through the base member and a second platform channel extending through the platform member, wherein the second platform channel is in fluid communication with the second base channel; and wherein circulating a treatment agent through the first channel, the second channel, and the nozzle interior comprises:
  passing treatment agent through the first base channel and the first platform channel; and
  passing treatment agent through the second base channel and the second platform channel.

* * * * *